United States Patent [19]

Klein et al.

[11] 4,178,373

[45] Dec. 11, 1979

[54] COAL TAR GEL COMPOSITION

[75] Inventors: Robert W. Klein, Blue Bell; Mary E. Foxx, Lansdale, both of Pa.

[73] Assignee: William H. Rorer, Inc., Fort Washington, Pa.

[21] Appl. No.: 935,341

[22] Filed: Aug. 21, 1978

[51] Int. Cl.$^2$ .................. A61K 31/615; A61K 31/00; A61K 31/05; A61K 47/00
[52] U.S. Cl. .................................... 424/233; 424/167; 424/196; 424/346; 424/317; 424/365; 424/358
[58] Field of Search ............... 424/167, 346, 196, 365, 424/233

[56] References Cited

U.S. PATENT DOCUMENTS

| | | | |
|---|---|---|---|
| 2,988,483 | 6/1961 | Barsky et al. | 424/365 |
| 2,988,484 | 6/1961 | Barsky et al. | 424/365 |
| 3,826,845 | 7/1974 | Suyama | 424/365 |
| 3,928,579 | 12/1975 | McShane | 424/167 |

*Primary Examiner*—Donald B. Moyer
*Attorney, Agent, or Firm*—James A. Nicholson

[57] ABSTRACT

Compositions effective for topically treating skin conditions, especially psoriasis and eczema which contains as an essential ingredient coal tar in a gel base.

7 Claims, No Drawings

COAL TAR GEL COMPOSITION

BACKGROUND OF THE INVENTION

The present invention relates to topical coal tar formulations in an anhydrous gel as a vehicle for the coal tar. Topical formulations containing coal tar as the active ingredient are extensively employed in the treatment of skin disorders, such as dermatitis. to be therapeutically effective, the active ingredient must be in a molecular dispersion to facilitate desired percutaneous absorption which is particularly important in achieving a therapeutic response for the management of psoriasis or eczema. Unfortunately, coal tar is practically insoluble in water. Certain organic solvents and solubilizers have been found to be good solvents for various fractions of coal tar. However, they have been found to be undesirable for commercial applications for reasons such as their high volatility and low boiling points, their disagreeable odor, and their untoward skin reaction. It is known to incorporate coal tar in an alcoholic gel base but such compositions have a drying effect on the skin and result in the production of denatured protein. Furthermore, various water-soluble emulsifiers and oil liquids or emolients have been suggested for use in preparing creams or lotions. However, because of the undesirably low solubility of the coal tar in such vehicles, higher levels of these materials in topical products are required thereby increasing their cost and also adversely affecting their cosmetic appearance.

Accordingly, in view of the above considerations, it is seen that a need exists for a suitable vehicle capable of solubilizing a sufficient amount of coal tar so that it may be employed in a topical formulation, while being dermatologically beneficial, stable and pharmaceutically acceptable.

DETAILED DESCRIPTION OF THE INVENTION

This invention relates to a novel and improved topical coal tar formulation in gel form for use in the treatment of skin disorders, such as dermatitis, and especially psoriasis and eczema. It has now been found that coal tar can be blended with an anhydrous gel system into a smooth and cosmetically elegant product through the utilization of a sarcosine compound as the co-blending agent. The topical formulations of this invention will preferably contain about 0.5–20% coal tar by weight based upon the entire formulation, preferably 2–10%; about 2–10% of a sarcosine compound, preferably about 2.5–4%; about 25–75% of a glyceryl ester and the remainder of the formulation being a gelling agent.

The term "coal tar" as used herein refers to whole crude coal tar, coal tar extract, coal tar filtrates, coal tar distillates, coal tar solution and the like.

The suitable anhydrous gelling agents which are useful in the formulation of coal tar therapeutic compositions used in the practice of this invention include acetone gels, glyceryl tris 12-hydroxy stearate, carboxy vinyl polymers (Carbopol), silica, methyl cellulose, hydroxy stearin, propylene carbonate, stearalaluminum hectorite, caboxy methyl cellulose, polyethylene gelled mineral oil, carboxy polymethylenes, hydroxy methyl carboxy ethyl cellulose, polyvinyl pyrolidine, and the like. Aluminum hydroxide and petrolatum are also useful materials in the preparation of gels herein. Mixtures of all of the above ingredients are obviously also contemplated herein.

Examples of useful sarcosine compounds which may be utilized include sarcosine, fatty acid sarcosines, i.e. cocoyl sarcosine, N-lauroyl sarcosine, N-myristoyl sarcosine, their organic salts and inorganic salts, especially sodium, potassium, calcium, and the like.

The glyceryl esters of fatty acids of 6 to 22 carbon atoms, particularly those having melting points in the range of about $-20$ to $+80°$ C. have been found to be most suitable. Typical representative examples of the glyceryl esters include the following:
glyceryl stearate,
glyceryl palmitate,
glyceryl laurate,
glyceryl cocoate,
glyceryl capric/caprylic ester,
glyceryl oleate,
glyceryl distearate,
glyceryl dipalmitate,
glyceryl dilaurate,
glyceryl stearate laurate,
glyceryl tristearate,
glyceryl tripalmitate,
glyceryl trilaurate,
glyceryl trimyristate,
glyceryl tricocate,
glyceryl trihydrogenated cocate,
glyceryl tricaproylate
glyceryl trioleate,
and the like. An especially good result is obtained using the readily available glyceryl capric/caprylic ester. "Cocoate" (cocate) is a coconut acid ester.

The topical formulation may contain pharmaceutically acceptable surfactants, wetting agents, preservatives, humectants, fillers, anti-oxidants, perfumes, cooling agents, such as menthol, soothing agents, such as camphor, or coloring agents.

It is particularly advisable to include a humectant such as glycerine, sorbitol, manitol or the glycols in the preparation of the therapeutic formulation.

PREPARATION OF THE THERAPEUTIC COMPOSITIONS

In order to prepare the compositions of this invention, the coal tar is initially blended with a sarcosine compound and a glyceryl ester. The mixture thus prepared may then be admixed in a conventional manner with an anhydrous gelling agent and other commonly available additive bases such as a humectant, perfume, etc. The concentration of the coal tar ranges from about 0.5–20% by weight of the total composition. The preferred composition has the coal tar in the range of from 2.0 to about 10%.

In addition, the therapeutic composition of this invention may include one or more additional beneficial compounds incorporated in the composition as described above. The compounds may function against any irritating action with highly sensitive skin, or may be effective against unrelated or remotely related disease conditions. If an additional active compound is used, it is preferred that the concentration of this compound not exceed 6% by weight of the total composition. Among the suitable additional compounds which may be added include resorcinol and its derivatives, salicylic acid, retenoic acid and its derivatives, and the like.

The therapeutic composition of this invention, prepared as described above, may be stored in laminated tubes or jars at room temperature for extended periods of time. No change in clinical effectiveness due to prolonged periods of storage has been observed.

The following Examples are illustrative of formulations of compositions according to this invention. Although the Examples utilize a named compound, the Examples are not intended to be limited to the specific compound named, but any member of the above-described group of compounds or combination thereof could be substituted therefor within the scope of this invention.

EXAMPLE 1

An emollient gel having the following composition:
coal tar (crude): 100 mg.
cocoyl sarcosine: 27.5 mg.
hexylene glycol: 120 mg.
salicylic acid: 30 mg.
benzyl alcohol: 2.5 mg.
Miglyol ® Gel*: 720 mg.

*Miglyol ® is a product of Kay Fries Co., consisting of a caprylic/capric triglyceride, stearalkonium hectorite and propylene carbonate.

was prepared as follows:

The coal tar (100 mg.) is mixed with cocoyl sarcosine (27.5 mg.) in hexylene glycol (20 mg.). Benzyl alcohol (2.5 mg.) and salicylic acid (30 mg.) are added and the mixing is continued. 720 mg. of Miglyol ® is then added with continuous stirring into the mixture. After continuous stirring a colored, transparent gel is obtained. No heating was required to obtain a uniform consistency. The resultant gel was filled into tubes.

Other gel preparations identical to that described immediately above are prepared by replacing the crude coal tar with the extract form, distillate, and the like or utilizing one of the previously mentioned gelling agents in place of the Miglyol ® gel.

EXAMPLE 2

An emollient gel having the following composition:
coal tar extract: 50 mg.
N-lauroyl sarcosine: 30 mg.
glyceryl capric/caprylic ester: 800 mg.
propylene glycol: 20 mg.
glyceryl tris 12-hydroxy stearate: 100 mg.
was prepared as follows:

Coal tar extract (50 mg.) ad N-lauroyl sarcosine (30 mg.) was stirred in a one liter flask containing 500 mg. of glyceryl capric/caprylate ester and 20 mg. of propylene glycol. After stirring 15 minutes, 400 mg. of glyceryl tris 12-hydroxy stearate was added and the stirring continued. A smooth opaque gel was obtained and filled into tubes.

EXAMPLE 3

A gel having the following composition:
coal tar (crude): 100 mg.
cocoyl sarcosine: 30 mg.
retenoic acid: 25 mg.
colloidal fumed silica (Cab-O-Sil ®): 60 mg.
glyceryl cocoate: 750 mg.
conservation agent: 5 mg.
glycerine: 30 mg.
was prepared as follows:

Crude coal tar (100 mg.) is admixed with glyceryl cocoate (750 mg.), retenoic acid (25 mg.) and glycerine (30 mg.).

The resultant mixture as stirred into a one liter beaker and 60 mg. of colloidal silica and 30 mg. of cocoyl sarcosine are added. The stirring continued for 30 minutes and a smooth uniform gel was obtained. A conservation agent (5 mg. of hydroxytoluene) was added and the resultant gel was filled into tubes.

We claim:

1. In a coal tar gel composition for topically treating eczema or psoriasis containing a gelling agent and from about 0.5 to about 20% by weight based on said composition of coal tar, the improvement which comprises including the combination of from about 2 to about 10% by weight based on said composition of a fatty acid derivative of sarcosine, said fatty acid having from 6 to 16 carbons, and from about 25 to about 75% by weight based on said composition of a glyceryl ester of a fatty acid having 6 to 22 carbon atoms; said glyceryl ester having a melting point of about −20° to +80° C.

2. The composition of claim 1 including a compound selected from the group consisting of resorcinol, salicylic acid and retenoic acid.

3. The composition of claim 1 wherein said glyceryl ester is the triglyceride of a mixture of caprylic and capric acids.

4. The composition of claim 1 wherein said fatty acid sarcosine is selected from the group consisting of cocoyl sarcosine, N-lauroyl sarcosine and N-myristoyl sarcosine.

5. The composition of claim 1 wherein said gelling agent is stearalkonium hectorite and propylene carbonate.

6. The composition of claim 1 which comprises from 2.0 to about 10% of coal tar, from 2.5 to about 4% cocoyl sarcosine, from 25 to about 75% of the triglyceride of a mixture of caprylic and capric acids, stearalkonium hectorite and propylene carbonate.

7. A method for treating eczema or psoriasis in humans which comprise topically administering an effective amount of the composition of claim 1.

* * * * *